(12) United States Patent
Tanaka et al.

(10) Patent No.: US 7,642,399 B2
(45) Date of Patent: Jan. 5, 2010

(54) MOUSE WITH DEFICIENCY OF GLUTAMATE TRANSPORTER GLAST FUNCTION

(75) Inventors: Kohichi Tanaka, Kanagawa (JP); Takayuki Harada, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/553,051

(22) PCT Filed: Apr. 13, 2004

(86) PCT No.: PCT/JP2004/005253

§ 371 (c)(1), (2), (4) Date: Aug. 8, 2006

(87) PCT Pub. No.: WO2004/092371

PCT Pub. Date: Oct. 28, 2004

(65) Prior Publication Data

US 2007/0011758 A1 Jan. 11, 2007

(30) Foreign Application Priority Data

Apr. 18, 2003 (JP) .............................. 2003-114793

(51) Int. Cl.
*A01K 67/027* (2006.01)
*C12N 15/00* (2006.01)
*C12N 5/00* (2006.01)

(52) U.S. Cl. ............................. 800/18; 800/24; 435/375

(58) Field of Classification Search ................... 800/18, 800/24; 435/375
See application file for complete search history.

(56) References Cited

FOREIGN PATENT DOCUMENTS

| JP | 64-33087 A | 2/1989 |
|---|---|---|
| JP | 10-033087 | 2/1998 |
| JP | 2002-369639 | 12/2002 |
| WO | WO 01/73020 A1 | 10/2001 |
| WO | WO 02/08415 A1 | 1/2002 |
| WO | WO 03/028444 A1 | 4/2003 |

OTHER PUBLICATIONS

Harada et al. PNAS 95:4663-4666; 1998.*
Watase et al. Eur. J. Neurosci. 10:976-988; 1998.*
Chitnis et al. J. Clin. Invest. 108(5):739-747; 2001.*
Harada, Takayuki et al, 1998, "Functions of the two glutamate transporters GLAST and GLT-1 in the retina", Proc. Natl. Acad. Sci., vol. 95, No. 8, pp. 4663-4666.
Martin, Keith R. G. et al., 2002, "Retinal Glutamate Transporter Changes in Experimental Glaucoma and after Optic Nerve Transection in The Rat", Investigative Ophthalmology & Visual Science, vol. 43, No. 7, pp. 2236-2243.
Naskar, Rita et al., 2000, "Concurrent Downregulation of a Glutamate Transporter and Receptor in Glaucoma", Investigative Ophthalmology & Visual Science, vol. 41, No. 7, pp. 1940-1944.
Taylor, Sara et al., 2003, "Glutamate stimulates neurotrophin expression in cultured Müller cells", Molecular Brain Research, vol. 111, No. 1-2, pp. 189-197.
Vorwerk, Christian K. et al., 2000, "Depression of Retinal Glutamate Transporter Function Leads to Elevated Intravitreal Glutamate Levels and Ganglion Cell Death", Investigative Ophthalmology & Visual Science, vol. 41, No. 11, pp. 3615-3621.
Araiki, Makoto, "New Glaucoma Treatment Methods—Development of Readily Applicable Glaucoma New Drugs for Lowering Intraocular Pressure, Improvement of Ocular Circulation and Neuroprotection," FY 1999 to FY 2001 Scientific Research Expense Subsity (Basic Research (A)(1) Working Paper, Mar. 2002, pp. 1-46 with English Translation of pp. 1 and 5.

* cited by examiner

*Primary Examiner*—Fereydoun G Sajjadi
(74) *Attorney, Agent, or Firm*—Foley & Lardner LLP (57) ABSTRACT

The present invention provides a GLAST knockout mouse lacking the function of an endogenous glutamate transporter GLAST gene, which shows: 1) an intraocular pressure within the normal range; and 2) a reduction in the number of cells in the retinal ganglions when compared with a wild-type normal mouse. Owing to the ocular properties, this knockout mouse is useful as a model for normal tension glaucoma. By using this knockout mouse, a compound useful for the treatment of normal tension glaucoma can be screened.

7 Claims, 5 Drawing Sheets

GLAST KO

WT

MOUSE WITH DEFICIENCY OF GLUTAMATE TRANSPORTER GLAST FUNCTION

FIELD OF THE INVENTION

The present invention relates to a GLAST knockout mouse deficient in the function of GLAST, which is one of glutamate transporters, and a process of producing the same. The present invention further relates to use of said knockout mouse as a model mouse of normal tension glaucoma and a method of screening a compound useful for the prevention and/or treatment of normal tension glaucoma using the knockout mouse.

BACKGROUND ART

Normal tension glaucoma is one type of glaucoma and is a disease recently getting attention particularly due to its high prevalence rate. In general, glaucoma is a disease characterized by elevated intraocular pressure (watery fluid pressure within the eyeball) resulting in compression of the optic nerve to produce atrophy and thus impairing the visual performance to narrow the visual field. If it is left untreated, the symptoms will eventually progress to blindness at a high risk. On the other hand, normal tension glaucoma is a pathological condition that mimics the findings on glaucoma with high intraocular pressure (optic atrophy and visual field defects), notwithstanding that the intraocular pressure lies within the normal range (usually 10-21 mmHg in human). In the developed countries, glaucoma is ranked as the second leading cause of vision loss next to diabetes mellitus. The prevalence of glaucoma in the population aged over 40 years is 3.5% in Japan and the number of patients is estimated to be about two million. According to a recent epidemiological survey, reportedly 70% of glaucoma is normal tension glaucoma. Because of slow progress and paucity of subjective symptoms, it is difficult to detect normal tension glaucoma at an early stage. At present, there is no decisive treatment except to further decrease the intraocular pressure.

In recent years, degenerative loss of retinal ganglion cells, namely, neuronal apoptosis, which is induced by a mild and chronic increase of glutamate level, is proposed to be one of the causes of glaucoma and diabetic retinopathy (Harada, T., et al. Proc. Natl. Acad. Sci. USA, 95, 4663-4666, 1998; Harada, C. et al., Neurosci. Lett., 292, 134-136, 2000).

In the mammalian central nervous system, glutamate is one of the main excitatory neurotransmitters and plays an important role in regulating a higher order function of the brain. On the other hand, it is known that glutamate causes neurotoxicity by an excessive rise, resulting in various neurodegenerative diseases or delayed neuronal cell death after cerebral ischemia. One of the mechanisms for regulating the level of this glutamate is glutamate transporters. Glutamate transporters are functional molecules, the main role of which is to take up glutamate once released from nerve endings into cells and maintain a low glutamate level at the synaptic cleft.

Currently, EAAC1, EAAT4 and EAAT5 (Kanai, Y. & Heidiger, M. A., Nature, 360, 467-471, 1992; Fairman, W. A., et al., Nature, 375, 599-603, 1995; Arrizal, J. E., et al., Proc. Natl. Acad. Sci. USA, 94, 4155-4160, 1997) present in neurons as well as GLT1 and GLAST (also referred to as GluT-1) present in glial cells (Pines, D. et al., Nature, 360, 464-467, 1992; Mukainaka et al., Biochimica et Biophysica Acta, 1244, 233-237, 1995; Tanaka, K., Neurosci. Res., 16, 149-153, 1993; Tanaka, K., Neurosci. Lett., 159, 183-186, 1993; Storck, T., et al., Proc. Natl. Acad. Sci. USA, 89, 10955-10959, 1992) are known as glutamate transporters in the mammalian brain. Abnormalities in the function of these glutamate transporters are known to be associated with various neurodegenerative diseases.

Under such circumstances, it has become clear that GLAST is present in Müller cells within the retina and retinal damages after ischemic load are exacerbated in GLAST knockout mice as compared to wild-type mice, based on the experiments using GLAST knockout mice (Watase, K. et al, Eur. J. Neurosci., 10, 976-988, 1998; Japanese Patent Laid-Open Application No. 10-33087). For this reason, it is suggested that GLAST present in Müller cells of the retina would be involved in the onset of glaucoma (Harada, T., et al., Proc. Natl. Acad. Sci. USA, 95, 4663-4666, 1998). However, unless ischemic load is applied, damage to the retinal tissue is not observed in this GLAST knockout mouse so that the mouse cannot be used as a model for normal tension glaucoma.

For the development of therapeutics for glaucoma and the elucidation of its onset mechanism, genetically chronic glaucoma model mice or high tension glaucoma model rabbits induced by water loading are already available as glaucoma model animals, but no model animal for normal tension glaucoma has ever been known heretofore. Also, there is no report to point out the relation of normal tension glaucoma to GLAST, and the onset mechanism of normal tension glaucoma yet remains unknown.

Accordingly, it is expected that if a model animal for normal tension glaucoma is obtained, the animal will be extremely useful for developing therapeutics effective for the treatment of said disease, establishing a remedy therefor and identifying the cause of said disease or its onset mechanism. However, any model animal for normal tension glaucoma is unknown at present and, such a model animal has been earnestly desired in the medical or pharmaceutical field.

DISCLOSURE OF INVENTION

The inventor has improved normal knockout mice (GLAST knockout mice), which conventionally exist and are deficient in the function of a glutamate transporter gene and as a result, could obtain improved GLAST knockout mice with the markedly reduced number of retinal ganglion cells due to degenerative loss of the cells, although the intraocular pressure is within the normal range. This knockout mouse was found to be useful as a model mouse for normal tension glaucoma.

Therefore, the present invention provides a GLAST knockout mouse deficient in the function of an endogenous GLAST gene, as a model for normal tension glaucoma and more particularly, a GLAST knockout mouse, in which 1) the intraocular pressure is within the normal range and 2) the number of cells in the retinal ganglions is reduced as compared to a wild-type mouse.

According to the present invention, the intraocular pressure of the GLAST knockout mouse is generally 21 mmHg or lower, for example, 10 to 21 mmHg. Also, the number of cells in the retinal ganglions is reduced by at least 20% in the GLAST knockout mouse, as compared to a wild-type mouse.

In the present invention, the genetic background of the GLAST knockout mouse is preferably the same or substantially the same as the genetic background of a C57BL J6 strain mouse, e.g., a C57BL/6J strain mouse.

Specifically, the present invention provides a GLAST knockout mouse carrying a neomycin-resistant gene inserted into the region of endogenous GLAST gene, for example, into the exon 6.

The present invention further provides use of such a GLAST knockout mouse as a model mouse for normal tension glaucoma.

In another aspect, the present invention provides a method of producing a GLAST knockout mouse deficient in the function of an endogenous GLAST gene. This production method comprises the following steps 1) to 6):

1) obtaining an ES cell from any mouse deficient in the function of one endogenous GLAST gene on the homologous chromosome, 2) obtaining a chimeric mouse carrying the ES cell using the cell obtained in step 1, 3) crossing the chimeric mouse obtained in step 2 with a normal C57BL/6 strain mouse to obtain a heterozygous knockout mouse, 4) crossing the heterozygous mouse obtained in step 3 with a normal C57BL/6 strain mouse to generate a heterozygous knockout mouse, 5) repeating the crossing described in step 4 at least a total of 5 times to generate a heterozygous knockout mouse thereby to bring the genetic background closer to the C57BL/6 strain mouse, and, 6) crossing the heterozygous knockout mice obtained in step 5 with each other to generate a homozygous or heterozygous GLAST knockout mouse.

In the production method of the invention, it is preferred to repeat the crossing described in step 4 at least a total of 9 times in step 5.

The present invention further includes the GLAST knockout mice produced by the production method of the invention, and the GLAST knockout mice thus produced can be used as model mice for normal tension glaucoma.

In yet another aspect, the present invention provides a method of using the GLAST knockout mice of the invention described above or the GLAST knockout mice produced by the production method of the invention described above, as model mice for normal tension glaucoma.

Therefore, the present invention provides a method of screening a compound useful for the prevention and/or treatment of normal tension glaucoma, which comprises using such GLAST knockout mice. More specifically, the screening method comprises:

1) administering a test compound to the GLAST knockout mouse of the invention, 2) administering a test compound to a wild-type mouse, 3) assessing the number or function of surviving optic nerve cells in each of the mice described above, prior to and after a given time period of the administration, and, 4) comparing the GLAST knockout mouse with the wild-type mouse in terms of the test results to determine effectiveness of the test compound.

According to the screening method of the invention, the number of nerve cells in the retinal ganglions is counted to assess the number of surviving optic neurons or the function of the optic neurons and in addition thereto, the assessment is conducted preferably by measurements of electroretinograms or visual evoked potentials (Porciatti et al., Vision Res., 39, 3071-3081, 1999), behavioral analysis such as the Visual Cliff test (Ma, L. et al., Neuron 36, 623-634, 2002), etc. in combination.

BEST MODE FOR CARRYING OUT THE INVENTION

In the present invention, mouse glutamate transporter GLAST (Glutamate/Aspartate Transporter) refers to a protein encoded by DNA strand having the base sequence represented by SEQ ID NO: 1 and having the amino acid sequence represented by SEQ ID NO: 2 (Tanaka, K., Neurosci. Lett., 159, 1803-186, 1993)). This protein is also termed GluT-1 in rat (Tanaka, K., Neurosci. Res. 16, 149-153, 1993; Storck, T., et al., Proc. Natl. Acad. Sci. USA, 89, 10955-10959, 1992). Both transporters are so-called counterparts.

The genomic structure of mouse GLAST has already been clarified and the details are described in Hagiwara, T., et al., Genomics, 33, 508-515, 1996. The structure of this gene is outlined in Table 1 and FIG. 1.

However, depending upon mouse strains, the mouse GLAST may undergo mutation in the encoded nucleotide sequence and amino acid sequence described above and its genomic sequence within the range to maintain the function, for instance, may undergo substitutions, deletions, additions or insertions of bases or amino acid residues. In the present invention, the mouse GLAST also includes these mutants such as a mutant with substitutions, deletions, additions or insertions of, e.g., 1 to 10, preferably 1 to 5 bases in the encoded nucleotide sequence described above, a mutant with substitutions, deletions, additions or insertions of, e.g., 1 to 10, preferably 1 to 5 amino acids in the amino acid sequence described above, etc.

TABLE 1

Exon-intron structure of mouse GLAST gene

| | Exon | | | Intron | | | Exon | |
|---|---|---|---|---|---|---|---|---|
| No. | Size (bp) | Sequence | Donor site | No. | Size (bp) | Donor site | Sequence | No. |
| 1 | 64, 128, 503 | TCAGAAAAG | gtaagcgca | 1 | ~1,500 | ccgctctag | TTGTCCTCT | 2 |
| 2 | 278 | TCATTGTGG aIleValG | gtgagtcgt | 2 | ~17,700 | tcccctcag | GTACAATCC lyThrIleL | 3 |
| 3 | 138 | TCGTCACAG euValThrG | gtaccggac | 3 | >13,000 | cttccccag | GAATGGCGG lyMetAlaA | 4 |
| 4 | 205 | TTTGATCAG pLeuIleAr | gtatgtcct | 4 | ~4,800 | tctttgcag | GAACATGTT gAsnMetPh | 5 |
| 5 | 43 | TTTAAACAG PheLysGln | gtaaatact | 5 | ~3,100 | atttttaag | TTTAAAACC PheLysThr | 6 |
| 6 | 293 | GATAATGTG lIleMetTr | gtatgtgtt | 6 | ~2,700 | ttgccgcag | GTATGCGCC pTyrAlaPr | 7 |
| 7 | 234 | CTCCTCAAG rSerSerSe | gtacgtgtg | 7 | 496 | tgccctcag | TTCTGCCAC rSerAlaTh | 8 |
| 8 | 195 | AACAATAAG eThrIleSe | gtacaaggg | 8 | ~3,300 | tgtcaacag | CATCACAGC rIleThrAl | 9 |
| 9 | 135 | CTGGTTTCT pTrpPheLe | gtgagtatt | 9 | ~2,300 | cacctgcag | GGACCGCCT uAspArgLe | 10 |
| 10 | 2414 | TACATTAAA | | | | | | |

Table 1 shows the sequencing of exon/intron splice site for GLAST gene. The nucleotide sequences for exons are represented by capitals and for introns by small letters.

In the present invention, the deficiency in the function of the glutamate transporter GLAST gene means that within the region of one or two endogenous GLAST genes present in one or two GLAST loci, functional GLAST remains unexpressed or expression of the GLAST gene is constantly suppressed, either by introducing a mutation into the region encoding its structure, e.g., into the exon, or by introducing a mutation into the region associated with expression of the GLAST gene, e.g., into the promoter or intron region. In any case, the term refers to such a state that one or two endogenous GLAST genes are substantially dysfunctional in vivo. In the present invention, therefore, the GLAST knockout mouse includes a homozygote deficient in the function of two endogenous GLAST genes and a heterozygote deficient in the function of one endogenous GLAST gene. In view of the effect of deficiency in the function of the gene, homozygous mice are preferred.

Such a deficiency in the function of the gene can be achieved by publicly known methods for generating knockout mice, e.g., a gene targeting strategy. Introduction of the mutation described above may also be substitutions of bases or deletions of bases in the GLAST gene region, or insertions of bases into the region.

In the present invention, the term "the same or substantially the same genetic background" is used to mean that all genotypes other than the targeted genotype (GLAST genotype) are the same by 99% or more. Specifically, this means that in EXAMPLES, F1 GLAST heterozygous knockout mice are backcrossed to normal C57B/L6 mice for at least 9 generations and the genes derived from the 129 strain have reached 1% or less than all genes.

1. GLAST Knockout Mouse of the Invention

The present invention provides a GLAST knockout mouse as a model mouse with normal tension glaucoma, which is deficient in the function of one or two endogenous GLAST genes on the homologous chromosome. Specifically, the present invention provides a GLAST knockout mouse, in which 1) the intraocular pressure is within the normal range and 2) the number of cells in the retinal ganglions is reduced as compared to a wild-type mouse. More particularly, the mouse preferably has the same or substantially the same genetic background as that of a C57BL/6 strain mouse, e.g., a C57BL/6J strain mouse.

The intraocular pressure of a wild-type normal mouse is generally 10 to 21 mmHg. The intraocular pressure of the knockout mouse of the present invention also lies within the normal range. The intraocular pressure may be outside the range above, but does not reach such a range as termed high pressure, e.g., 30 mmHg or higher. The intraocular pressure in mice can be determined by using, e.g., an electronic tonometer.

Furthermore, in the knockout mouse of the present invention, the number of nerve cells in the retinal ganglions is reduced by at least 20%, preferably at least about 50%, as compared to the number in normal mouse. The reduction in the number of nerve cells in the retinal ganglions can be microscopically determined by conventional histochemical means, for example, by hematoxylin/eosin staining using a section.

Further in the knockout mouse of the present invention, a reduced b-wave, which is a sort of potential change in the retina by photic stimulation, is also noted, when compared with a wild-type normal mouse. The b-wave reflects an action potential in the inner retinal layer containing Müller cells in which GLAST exists, suggesting that a mechanism regulating glutamate levels by GLAST would have an important role also in visual transmission (Harada, T., et al., Proc. Natl. Acad. Sci. USA, 95, 4663-4666, 1998).

This reduction in the number of nerve cells in the retinal ganglions can be regarded as neurodegeneration or neuronal apoptosis. In general, optic disc atrophy or deficits of the retinal nerve fibers are observed in glaucoma including normal tension glaucoma. Currently, the final clinical picture of glaucoma is thought to be retinal ganglion cell death.

Thus, taking into account these ocular properties of the GLAST knockout mouse of the present invention, namely, the intraocular pressure within the normal range and the reduction in the number of cells in the retinal ganglions, the mouse can be used as a model mouse for normal tension glaucoma.

2. Production of GLAST Knockout Mouse of the Invention

In a second aspect, the present invention provides a method of producing the GLAST knockout mouse of the present invention. This method comprises the following steps 1) to 6):

1) obtaining an ES cell from any mouse, which is deficient in the function of one endogenous GLAST gene on the homologous chromosome,
2) obtaining a chimeric mouse carrying the ES cell using the cell obtained in step 1,
3) crossing the chimeric mouse obtained in step 2 with a wild-type C57BL/6 strain mouse to generate a heterozygous knockout mouse,
4) crossing the heterozygous mouse obtained in step 3 with a wild-type C57BL/6 strain mouse to generate a heterozygous knockout mouse,
5) repeating the crossing described in step 4 at least a total of 5 times to generate a heterozygous knockout mouse thereby to bring the genetic background closer to the C57BL/6 strain mouse, and,
6) crossing the heterozygous knockout mice obtained in step 5 with each other to generate a homozygous or heterozygous GLAST knockout mouse.

In step 5 described above, the crossing is repeated preferably at least 9 times in total.

Basically, publicly known methods for producing knockout mice, e.g., gene targeting strategy, gene trapping strategy, etc., can be used to produce the GLAST knockout mouse of the present invention available as a model for normal tension glaucoma. Basic methods for producing knockout mice are not particularly limited, as far as the GLAST gene can be disrupted and mice whose surviving and reproductive potentials are not lost are obtained. For the methods of producing knockout mice, reference can be made to, e.g., "Jikken-Igaku-Bessatsu, Kaitei-Idenshi-Kogaku Handbook (Handbook of Genetic Engineering), 3rd revised version", edited by Masami Muramatsu and Tadashi Yamamoto (published by Yodosha Co., Ltd., 1996) or "Jikken-Igaku-Bessatsu, The Protocol Series: Latest Technology of Gene Targeting", edited by Takeshi Yagi (published by Yodosha Co., Ltd., 2000), which can be applied to carry out the present invention.

First, the steps 1 through 4 described above can be performed in accordance with conventional methods, e.g., the gene targeting strategy. These steps are disclosed also in Japanese Patent Laid-Open Application No. 10-33087 by the research group of the present inventors and Watase, K. et al, Eur. J. Neurosci., 10, 976-988, 1998.

Heretofore, homozygous or heterozygous GLAST knockout mice obtained by mating female and male of the heterozygous GLAST knockout mice obtained in step 4 described above are already disclosed but in this type of GLAST knockout mice, no significant change was noted in the number of cells in the retinal ganglions, when compared with wild-type normal mice; a decrease in the number of cells in the retinal ganglions was observed only after transient ischemia was achieved by instilling sterile saline into the eye of the GLAST knockout at 150 cm $H_2O$ pressure for 60 minutes (Harada, T., et al., Proc. Natl. Acad. Sci. USA, 95, 4663-4666, 1998).

For these reasons, such GLAST knockout mice hitherto known cannot be used as a model for normal tension glaucoma.

According to the production method of the present invention, such conventional GLAST knockout mice are further improved, whereby the GLAST knockout mouse of the present invention with normal tension glaucoma described above can be produced.

Hereinafter, the method for producing the knockout mouse of the present invention will be described below, taking as an example the gene targeting strategy which is a standard method for producing a knockout mouse.

Step 1

(1) Preparation of Targeting Vector

According to the gene targeting strategy, in order to disrupt the GLAST locus on the chromosome in mouse ES cells, a targeting vector is used to introduce a mutation into the locus.

In order to render the function of GLAST gene defective, bases are deleted, point mutation is introduced or other genes are inserted into any part of the GLAST gene, e.g., one or more exon regions. Generally in order to select the endogenous GLAST gene-disrupted ES cells more readily, it is preferred to insert a selection marker gene.

As such a gene, a marker gene for positive selection, for example, a neomycin (neo)-resistant gene can be employed. This neomycin-resistant gene enables to screen the objective gene by using the neomycin analog G418. Also, a marker gene for negative selection can also be used to screen and remove the objective gene. Examples of such genes used include thymidine kinase (tk) gene (using ganciclovir, FIAU, etc. as a screening marker, a non-homologous recombinant is screened and removed by the sensitivity thereto) and diphtheria toxin A fragment (DT-A) gene (a non-homologous recombinant is screened and removed by diphtheria toxin expressed by DT-A). Alternatively, a combination of the foregoing can also be used for positive/negative selection. It is preferred to insert, e.g., neomycin-resistant gene and diphtheria toxin A fragment gene (Yagi, Nada, Watanabe, et al., Analytical Biochemistry, 214, 77-86, 1993), or neomycin-resistant gene and thymidine kinase gene (Mansour, Thomas and Capacchi, Nature, 336, 348-352, 1988).

In the gene sequence, a site to introduce a mutation, for example, a site to insert the marker gene described above is not particularly limited, so far as it is a site that function of the gene is lost, but the site is usually an exon site.

Figure 1:
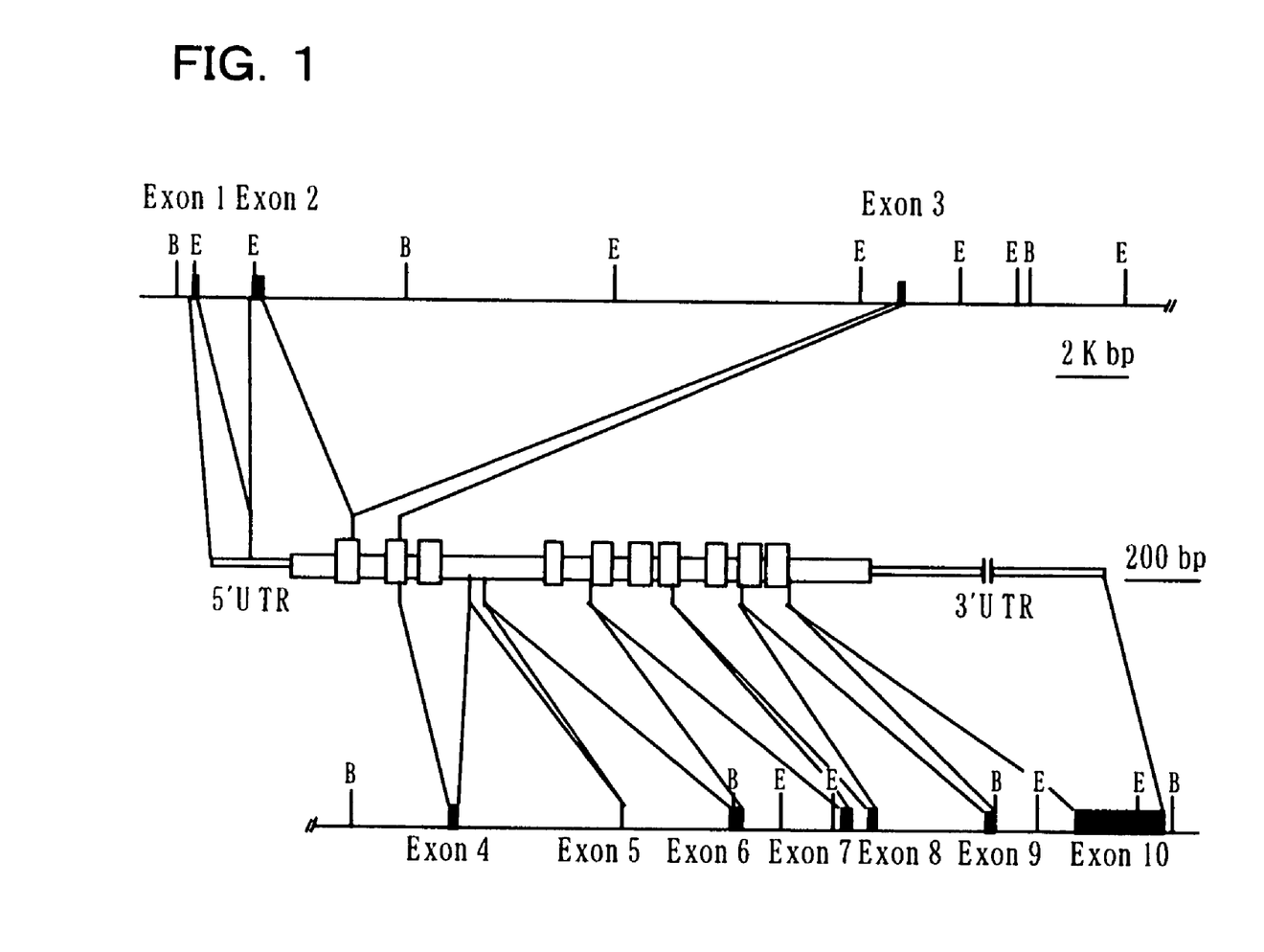
FIG. 1 shows an outlined genomic structure (restriction enzyme sites and exon sites) of mouse GLAST gene. In the Figure, the restriction enzymes involved in the restriction sites shown by the respective symbols are as follows. E: EcoRI and B: BamHI. The black box designates Exons 1 to 10.

The genomic structure (restriction enzyme map and each exon-intron splice point) of GLAT gene are already known (Hagiwara, T., et al., Genomics, 33, 508-515, 1996), which structure is outlined in FIG. 1 and Table 1. The mouse GLAST gene comprises 10 exons. It is preferred to insert a marker gene into any one of the exons so as to cause deficiency of the gene.

In order to disrupt the function of the gene as described above, homologous recombination with the target gene is available so that a targeting vector (DNA for homologous recombination) capable of introducing a mutation into the target gene can be prepared by conventional DNA recombinant techniques, for example, PCR or site-specific mutagenesis, based on the GLAST-encoding nucleotide sequence (SEQ ID NO: 1) and information of genomic sequence of the GLAST gene (Hagiwara, T., et al., Genomics, 33, 508-515, 1996).

For example, a DNA molecule containing the entire gene or its fragment is isolated in a conventional manner from the mouse strain, from which ES cells used are derived. The DNA molecule may be a DNA molecule containing the entire GLAST gene or further containing the 5' upstream region and/or the 3' downstream region of the gene, in addition to the entire gene.

Next, a modified DNA molecule is prepared from the resulting DNA molecule by introducing a desired mutation into the site corresponding to the mutation site in the gene, e.g., by introducing the marker gene described above. Modification of the base sequence can be made by conventional recombinant DNA techniques such as ligation of DNA molecules amplified by PCR, site-specific mutation, etc. In constructing such a targeting vector, plasmid vectors commercially available for targeting vector construction may also be used.

(2) Introduction of Targeting Vector into ES Cells and Homologous Recombination with Endogenous GLAST Gene The thus obtained targeting vector is introduced into mouse embryonic stem cells (ES cells) to perform homologous recombination. Introduction of the targeting vector into ES cells can be made by conventional DNA transfection techniques, e.g., electroporation, lipofection, etc. In the targeting vector-transfected cells, homologous recombination occurs between the GLAST gene on the chromosome and the counterpart on the targeting vector so that the modified base sequence in the targeting vector, e.g., a marker gene is introduced into the endogenous gene. As a result, the ES cells are deficient in the function of endogenous GLAST gene and at the same time contains, e.g., the marker gene. The cells where the targeting vector is introduced are then screened by the screening function of, e.g., the marker gene, or in a conventional manner such as southern blotting for confirming homologous recombination, PCR, etc. to obtain ES cells deficient in the function of GLAST gene (hereinafter referred to as recombinant ES cells). By such homologous recombination, usually ES cells with disrupted GLAST gene only on one homologous chromosome are obtained.

Mouse ES cells used are generally 129 ES cells already established. In addition, ES cells are established by publicly known methods (Teratocarcinomas and Embryonic Stem Cells: A Practical Approach (Robertson, E. J., ed.), IRL press, Oxford, 1987) using C57BL/6 or BDF1 strain mice (F1 mice obtained by crossing C57BL6 with DBA/2). These ES cells may also be used. Preferably, 129-derived ES cells are used.

Steps 2 and 3

Production of Heterozygous GLAST Gene Knockout Mouse in the F1 Generation

Next, the resulting recombinant ES cells are developed to generate a chimeric mouse. For this purpose, the recombinant ES cells are injected into normal mouse embryos at the blastocyst stage, the 8-cell stage, etc. by microinjection or aggregation. The thus obtained chimeric embryos are transplanted to the uterine horn of a pseudopregnant female mouse. This transplanted mouse can be bred in a conventional manner and allowed to deliver the offspring of the chimeric mouse. Preferably, the recombinant ES cells are injected into the embryos of C57BL/6 strain mice.

In general, this chimeric mouse comprises cells derived from the recombinant ES cells and normal cells as its somatic cells and germ cells. By crossing the chimeric mouse with a wild-type mouse of a proper line, preferably a C57BL/6 strain mouse, e.g., a C57BL/6J strain mouse, heterozygous F1 offspring are obtained. Usually, a male chimeric mouse is mated with a female wild-type mouse to generate heterozygous offspring of the F1 generation. If the germ cells of the chimeric mouse used for the mating are derived from the recombinant ES cells described above, i.e., cells carrying the disrupted endogenous GLAST gene present on one of the homologous chromosomes, then desired heterozygous F1 mice deficient in the function of the gene can be obtained.

In the step described above, to generate the heterozygous F1 mice with high efficiency, for example, normal host embryonic cells derived from a mouse having a coat color different from the mouse of the recombinant ES cell origin are used in combination, e.g., in the preparation of chimeric embryos. By inspection of the coat color, a chimeric mouse showing a higher rate of the recombinant ES cells in vivo or a heterozygous F1 mouse can be easily screened.

It can be confirmed by analysis of DNA extracted from the tail using southern blotting or PCR whether a desired genotype is achieved in the F1 generation or not.

Steps 4, 5 and 6

(1) Obtaining of GLAST Gene Knockout Mouse of the Invention

In the present invention, it is preferred to bring the genetic background of the GLAST gene knockout mouse as closer as possible to the C57BL/6 strain mouse. For this purpose, the F1 heterozygous mouse produced as described above is further crossed with a C57BL/6 strain mouse, e.g., a C57BL/6J strain mouse and the delivered heterozygous mouse is again crossed with a C57BL/6 strain wild-type mouse. The crossing procedures are repeated normally at least 5 times in total, preferably at least 9 times and more preferably at least 15 times. Finally by crossing female and male of the resulting heterozygous mice with each other, the homozygous or heterozygous knockout mouse of the present invention deficient in the function of GLAST gene can be obtained. In view of the effect of deficiency in the function of glutamate transporter gene, homozygous mice are preferred.

Whether a desired genotype is achieved in the respective generations or not may be determined by conventional techniques, including southern blotting, PCR, base sequencing, etc., as described above.

Once the knockout mice of the present invention which can be produced as above are obtained in the combination of males and females, subsequently knockout mice having the same genotype can be readily obtained in the number as required, by appropriately breeding the offspring, depending on necessity.

(2) Analysis of the Retina and Intraocular Pressure in GLAST Knockout Mouse of the Invention Finally, it is confirmed on the homozygous or heterozygous GLAST knockout mice produced as described above that the intraocular pressure is within the normal and nerve cells in the retinal ganglions are reduced. When these ocular properties cannot be confirmed, the crossing described in step 5 is repeated so that the knockout mouse of the present invention satisfying the properties above can be obtained.

The intraocular pressure of the GLAST knockout mouse of the present invention is generally about 21 mmHg or lower, for example, about 10-21 mmHg. This intraocular pressure range may be somewhat varied depending upon the strain of mice, from which the ES cells used are derived, or the strain of mice from which the normal embryos used to prepare chimeric embryos are originated. Even in view of the foregoing, the intraocular pressure should be not higher than 30 mmHg.

In the GLAST knockout mouse of the present invention, the number of nerve cells in the retinal ganglions is reduced by at least 20%, preferably at least about 50%, as compared to a wild-type mouse.

Hereinafter, a method for measurement of the number of cells in the retinal ganglions and a method for measurement of the intraocular pressure will be described by way of examples but is not deemed to be limited thereto and any conventional publicly known methods may also be used. Reference may be made to, e.g., Harada, T., et al., Proc. Natl. Acad. Sci. USA, 95: 4663-4666, 1998 or Harada, C., et al., Neurosci. Lett., 292, 134-136, 2000.

In these measurements, the wild-type normal mice delivered simultaneously with the homozygous or heterozygous knockout mice of the present invention described above or mere normal (wild-type) C57BL/6 strain mice can be used as control mouse against these mice of the present invention.

In addition to the control mouse described above, the measurements are also applied, if necessary, to the homozygous or heterozygous GLAST knockout mice obtained by mating the F1 heterozygous knockout mice described above or their females and males, heterozygous knockout mice obtained during backcrossing, and so on.

Measurement of the Number of Cells in the Retinal Ganglions:

The number of cells in the mouse retinal ganglion can be measured by conventional histochemical means or retrograde labeling.

(a) Method using Pathological Section

1) Test mice are anesthetized to keep them still and perfused with 4% paraformaldehyde/PBS solution to fix.

2) Eye globes are enucleated and fixed at 4° C. in the same solution for further 2 hours.

3) After the eye globes are embedded in paraffin, sections, e.g., 7 μm thick sections of the retina are prepared.

4) The sections are stained with hematoxylin/eosin and the number of cells in the ganglion was counted under microscope on the cross-section containing optic nerves.

(b) Method using Retrograde Labeling

1) Following anesthetic sedation, the mouse is placed in a stereotaxic head frame.

2) After spraying ethanol under microscope, an incision is made with scissors along the midline of the head, exposing the skull.

3) After confirming sutures and blood vessels, holes for operation are drilled with a grinder and through the holes, e.g., fluorescent dye Fluoro-Gold (general name, aminostilbamidine; Molecular Probes, Inc.) or a carbocyanine fluorescent dye such as DiI (general name, 1,10-dioctadecyl-3,3,30,30-tetramethylindocarbocyanine perchlorate; Molecular Probes, Inc.) is injected into the superior colliculi.

4) After the skin is fastened with clips, an antihypnotic is intraperitoneally injected and the recovery is ensured.

5) Following normal breeding for 7 days after the operation, the treated mice are anesthetized with ether resulting in death and eye globes are enucleated. The anterior part of the eye is removed.

6) The posterior part of the eye including the retina is placed in a solution of 4% paraformaldehyde and fixed at 4° C. for 20 minutes.

7) The retina is taken out and a whole-mount preparation is made.

8) After photographs are taken with a fluorescence microscope, the number of fluorescence-labeled cells in the retinal ganglions is counted.

Any anesthetic can be used in such a concentration range that mice are not dead, as far as it is an anesthetic available for ordinary animal tests. For example, a 1:1 mixture of ketamine (10 mg/ml)/medetomidine (1 mg/ml) (0.15-0.2 ml/mouse) may be employed. In this case, the animal can be awakened with atipamezole (5 mg/ml) (0.15-0.2 ml/mouse).

Measurement of Intraocular Pressure:

1) Mice are anesthetized with sedation in a conventional manner, as described above.

2) The intraocular pressure of sedated mice is measured with an electronic tonometer (e.g., TONOPEN XL, manufactured by Medtronic Solan, US).

To assess the visual function or the function of optic nerve cells, electroretinograms (ERG) may be measured. This is to measure an electric response obtained from the retina caused by photic stimulation and is a good indicator representing the activity of neuronal transduction of optic nerve cells in vivo. For more details, reference is made to "Gendai-No-Me-Ka-gaku (Modern Textbook of Ophthalmology)," revised 8th edition (edited by Takashi Tokoro, Atsushi Kanai, published by Kanehara & Co., Ltd.), "Shino-Kyoseigaku (Visual Orthotics), revised 2nd edition" (edited by Toshio Maruo, published by Kanehara & Co., Ltd.), or Non-Patent Literature 1 (Harada, T., et al. Proc. Natl. Acad. Sci. USA, 95: 4663-4666, 1998).

The measurement method is briefly explained below

1) Mice are anesthetized in a conventional manner and secured with a head holder to fix the position of each mouse.

2) The pupils are dilated by administration of 0.5% phenylephrine and 0.5% tropicamide.

3) A carbon fiber electrode is placed on the corneal surface and a reference electrode is attached subcutaneously on the forehead.

4) Mice undergo dark adaptation for 30 minutes.

5) Test flashes of 10 μs duration are given with an intensity of 0.6 or 1.2 J for retinal stimulation, using the photostimulator (SLS-3100, Nihon Kohden, Japan) were presented (SLS-3100, Nihon Kohden).

6) A bandpass frequency is set at 50 to 1000 Hz and 1 to 1000 Hz on the amplifier (MEB-5304, Nihon Kohden), and the potentials generated (in the case where each oscillatory potential OP and the a-wave and b-wave are measured, respectively.) are amplified.

7) The two responses are averaged and recorded.

8) The a-wave, b-wave and oscillatory potentials are analyzed as data.

3. Method of Screening a Compound useful for the Prevention/Treatment of Normal Tension Glaucoma The knockout mouse of the present invention can be used for screening a compound useful for the prevention/treatment of normal tension glaucoma, especially a compound useful for preventing the death or degeneration of optic nerve cells including retinal ganglions, or for preventing diminished activity of the function, or a compound useful for recovering optic nerve cells or their function.

Therefore, the present invention provides a method of screening a compound useful for the prevention/treatment of normal tension glaucoma and comprises:

1) administering a test compound to the homozygous or heterozygous GLAST knockout mouse of the present invention, 2) administering a test compound to a wild-type normal mouse, 3) assessing the number or function of surviving optic nerve cells in each of the mice described above, prior to and after a given time period of the administration, and, 4) comparing the GLAST knockout mouse with the wild-type mouse in terms of the test results to determine effectiveness of the test compound.

Whether a test compound is useful for the prevention/treatment of normal tension glaucoma or not can be determined by examining whether the compound can improve a sign characteristic of glaucoma. For example, after a test compound is administered, the number of nerve cells in the retinal ganglions is counted; when the number is recovered by at least 10%, preferably by at least 20% and more preferably by at least 30%, as compared to the control mouse, the test compound can be judged to be medically effective. Furthermore, after a test compound is administered, the retinal potentials are measured; when the amplitude of, e.g., b-wave or oscillation potential is recovered by at least 10%, preferably by at least 20% and more preferably by at least 30%, as compared to the control mouse, the test compound can be judged to be medically effective.

Figure 4:
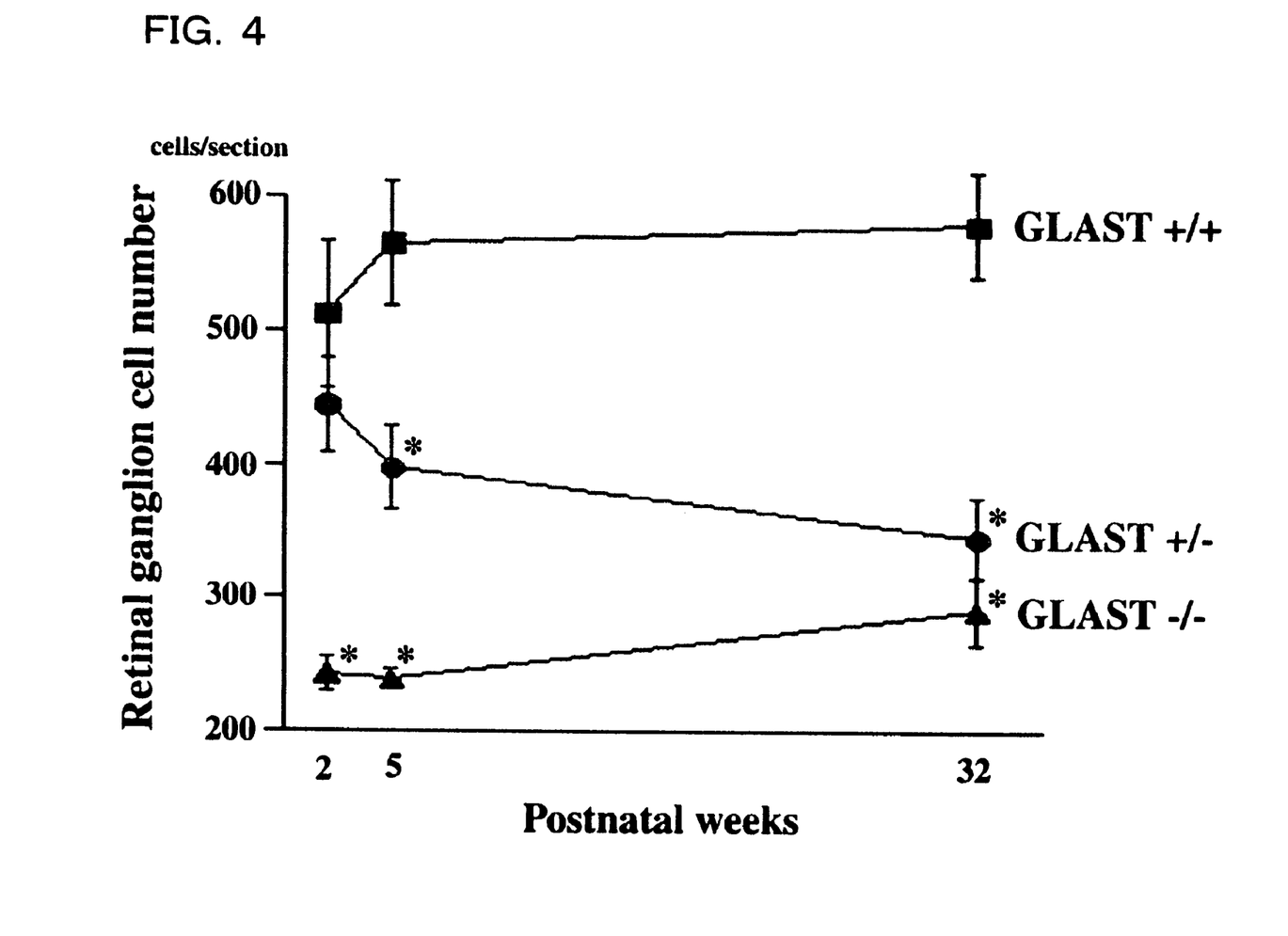
FIG. 4 shows the number of cells in the retinal ganglions in homozygous GLAST knockout mice (GLAST−/−), heterozygous GLAST knockout mice (GLAST+/−) and wild-type normal mice (GLAST+/+), at the age of given weeks after birth. The number of these cells was determined by counting the number of nerve cells in the pathological section of retinal ganglions after hematoxylin/eosin staining. The ordinate represents a mean cell count per section from 3 to 22 sections. The abscissa represents the age of weeks after birth.

In the heterozygous knockout mouse of the present invention, the number of cells in the retinal ganglions is found to be gradually reduced with the age of weeks after birth (FIG. 4). Accordingly, in one embodiment of the screening method described above, a compound which prevents a reduction of the number of cells in the retinal ganglions with passage of time can also be screened by 1) regularly administering a test compound to a group of heterozygous knockout mice immediately after birth but administering no test compound to another group of heterozygous knockout mice, 2) counting the number of cells in the retinal ganglions at the age of respective weeks, and 3) comparing the two groups.

The test compound which can be used includes, in addition to naturally occurring and synthetic compounds, optional compounds such as animal and plant extracts, fermentation products, peptides, proteins, nucleic acid molecules, etc. The test compound may be a gene vector for expressing a desired protein. For administration of the test compound, a variety of routes may be attempted as far as properties of the test compound permit, and the compound may be administered, e.g., as eye drops or by oral administration. Dosing period or dosing mode can be chosen so as to maximize the effect of a test compound. Kind and dosing of such a test compound may also be in accordance with conventional methods in the pharmaceutical field or medical field.

Furthermore, the GLAST knockout mouse of the present invention can be crossed with other strain of knockout mouse or other strain of disease model mouse to generate a novel disease model mouse. The present invention also includes such use of the GLAST knockout mouse of the present invention.

EXAMPLES

Hereinafter, the present invention is described in more detail by referring to EXAMPLES but is not deemed to be limited thereto.

Example 1

Figure 2:
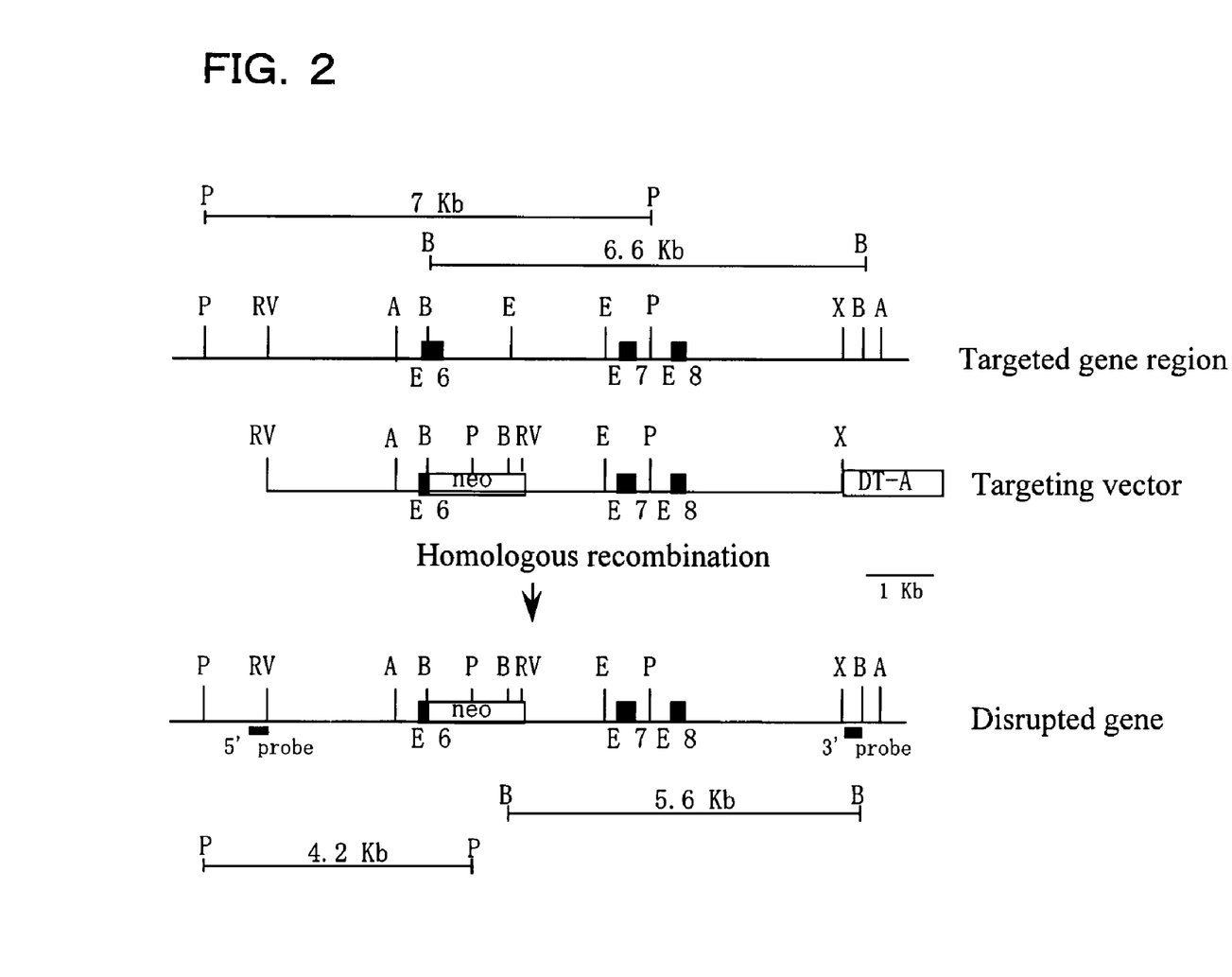
FIG. 2 shows the structures of the targeted gene region intended to disrupt for the functional deficit of mouse GLAST gene (upper column), the targeting vector used (middle column) and the GLAST gene disrupted (lower column), in EXAMPLE 1. In the Figure, the restriction enzymes involved in the restriction sites shown by the respective symbols are as follows. P: PvuII, RV: EcoRV, B: BamHI, E: EcoRI and X: XhoI. The black box designates Exons 6 to 8 (E6 to E8). The symbol neo designates neomycin-resistant gene and DT-A designates diphtheria toxin A fragment gene.

Production of Mouse Deficient in the Function of GLAST (GluT-1) Gene (1) Preparation of DNA for Homologous Recombination in Mouse GLAST (GluT-1) Gene DNA Genomic DNA extracted from the liver of a 129SV mouse was partially digested with restriction enzyme Sau3AI. For the resulting genomic library lambda FIXII, hybridization was carried out using as a probe a partial sequence of cDNA for mouse GLAST (GluT-1) gene. Colonies of $1 \times 10^6$ were screened to give 26 positive clones. After the clones were incompletely digested with restriction enzymes EcoRV and XhoI, the full length genomic DNA of 9 kbp containing exons 6 to 8 was subcloned thereto (FIG. 2, upper column). Next, in order to disrupt the GLAST (GluT-1) gene, a 1.5 kbp region following the BamHI site in exon 6 was made defective, and the neomycin-resistant gene was inserted therein and a diphtheria toxin A fragment gene was further inserted into the downstream of exon 8 (FIG. 2, middle column). The homologous region with the genomic DNA was constructed to be 2.5 kb length at the upstream of the neomycin-resistant gene and 5 kb length between the neomycin-resistant gene and the diphtheria toxin A fragment gene. The thus obtained construct was inserted into pBluescriptSK and digested with restriction enzyme NotI for linearization at the time of transfer into ES cells, whereby a targeting vector (DNA: pGluT1NeoDT for homologous recombination) was obtained (FIG. 2, middle column).

(2) GLAST (GluT-1) Gene Deficiency in ES Cells by Transferring DNA for Homologous Recombination Seventy-five (75) micrograms of DNA for homologous recombination was suspended in buffer for electroporation (137 mM NaCl, 2.7 mM KCl, 10 mM $Na_2HPO_4$, 1.8 mM $KH_2PO_4$) containing $3 \times 10^7$ mouse ES cells (E14 strain), and a gene transfer was performed under the conditions of an electric field strength of 210 V/cm and a capacitance of 500 µF. After 24 hours of the transfer, selection culture was performed with 250 µg/ml of G418 (Geneticin, GIBCO BRL).

After 192 hours of the gene transfer, G418 resistant colonies were transferred into a 96-well microplate (FALCON 3077) charged with 60 µl of Tris-EDTA solution (solution composed of 10 mm Tris-HCl, pH 8.0 and 1 mm EDTA, pH 8.0) using a micropipette, and treated for several minutes to prepare single cells by pipetting. These cells were transferred to a 24-well plate (FALCON 3047) and the culture was continued. The colonies collected were those having the major axis reaching at least ½ of the inner diameter of the microchip and the number of cells at this stage showed $1 \times 10^4$ to $10^5$. The number of surviving cells after the electroporation was $6.0 \times 10^7$. The number of G418-resistant colonies was $2.4 \times 10^2$, which was $1/2.5 \times 10^5$ of the number of surviving cells.

At the stage when cells on the 24-well plate reached confluent by culturing for 3 to 4 days, the cells were treated with 0.25% trypsin at 37° C. for 5 minutes and sequentially cultured in a 35 mm (FALCON 3001) or 60 mm (FALCON 3002) Petri dish to effect proliferation of the cells. The ES cells were all cultured on feeder cells. The homologous recombinants were confirmed by southern blotting as described below.

The genomic DNA for southern blotting analysis was extracted from the G418-resistant cells, digested with restriction enzyme PvuII and then subjected to the analysis using as a probe 0.5 kb of ApaI-EcoRV fragment in intron 5. The homologous recombinant containing the disrupted allele (FIG. 2, lower column) and non-homologous recombinant were confirmed by detecting the bands of 4.2 kb and 7 kb, respectively. The number of homologous recombinant colonies was 1 (2B7) out of 242 colonies of the G418 resistant colonies.

(3) ES Cells and Method of Culturing

The ES cells used were those of the E14 strain derived from 129/SvJ mouse blastocysts. The ES cells were cultured in SCM culture medium (Robertson, Teratocarcinomas and Embryonic Stem Cells: A Practical Approach, 1987), namely, Dulbecco's modified Eagle's medium (DMEM, 11960-010, GIBCO) supplemented with 15% fetal calf serum (FCS), 0.1 mM 2-mercaptoethanol, a nucleic acid mixture solution, a non-essential amino acid solution and $10^3$ unit/ml of LIF (AMRAD).

Also, the mouse fetal fibroblasts used as feeder cells for the ES cells were cultured in DMEM containing 10% FCS. The preparation and culture of the mouse fetal fibroblasts were carried out by the following procedures. After ICR mouse fetuses with a fetal age of 13-14 days were aseptically collected and washed with phosphate buffered physiological saline containing no calcium or magnesium (PBS-), the hearts, livers and bowels were removed using forceps and morcellated with ophthalmic scissors. Subsequently, the morcellated pieces were then treated at room temperature for 20 minutes with PBS-containing 0.25% trypsin and 0.04% EDTA (hereinafter referred to as TE solution) to obtain a cell suspension.

After the cell suspension was centrifuged at 1500 rpm for 5 minutes, the supernatant was removed off and the cells were suspended in DMEM supplemented with 10% FCS, which was allowed to settle for 2 minutes. The suspension, from which the tissue fragments precipitated at the bottom had been removed, was then transferred to a 100×20 mm Petri dish for tissue culture (FALCON 3003), and provided for culture under the conditions of 37° C. in 5% $CO_2$ and 95% air. On the following day, the cell suspension was washed once with PBS-, followed by culturing. Subculture was performed at 3 to 4 day intervals and the cells from the 1st to 3rd generation of subculture were subjected to mitomycin treatment for use as feeder cells.

The mouse fetal fibroblasts, which had grown to confluence, were treated for 3 to 4 hours with 75 μl of 2 mg/ml mitomycin C, washed 3 times with PBS-, and then treated with TE solution at room temperature for 3 minutes to detach the cells. After centrifugation, the number of cells was adjusted to $5×10^5$/ml, and 3 ml each was dispensed onto 60×10 mm gelatin-coated dishes (FALCON 3002). The feeder cells prepared in the manner described above were used within one week. Subculture of the ES cells was carried out by treating with TE solution at room temperature for 5 minutes, followed by dispersing the ES cells as single cells by pipetting and then inoculating $4×10^5$ cells onto a layer of feeder cells.

The culture medium was replaced at 24 hour intervals, and the subculturing interval was 56 to 64 hours. For cryopreservation, $1×10^6$ cells were suspended in SCM and transferred to a tube for lyophilization (2 ml, FALCON 4818) and 0.5 ml of freezing medium (DMEM supplemented with 20% DMSO) was dropwise added thereto. Thereafter, the mixture was allowed to stand overnight at −80° C. and then stored in liquid nitrogen.

(4) Production of Chimeric Mouse by GLAST (GluT-1) Gene-Deficient ES Cells (a) Injection of GLAST (GluT-1) Gene-Deficient ES Cells into Blastocyst The ES cells were injected into the blastocysts from C57BL/6J mice, and the resulting host embryos were then transferred into the uterine horn of pseudopregnant mice to obtain offspring. The host embryos were collected on the 4th day of natural mating by flushing the uterus with HEPES-buffered Whitten's medium. The ES cells used for the injection had been subjected to treatment with TE solution on the 2nd or 3rd day of subculture and then placed in gelatin-coated dishes for 30 minutes to remove the feeder cells. The ES cells were then placed on ice until they were provided for micromanipulation.

The injection pipette for the ES cells was prepared from a glass capillary (NARISHIGE) having an outer diameter of 1 mm by thinly pulling the capillary using a microelectrode puller (NARISHIGE, PN-3), polishing the tip with a grinder (NARISHIGE) to an inner diameter of about 20 μm, and finally sharpening the tip with a microforge (De Fonburun). The embryo-holding pipette was prepared by using a microforge to cut a glass capillary pulled by the procedure above at a section in a 50-100 μm outer diameter, and then further finishing the aperture to 10-20 μm.

Both of the injection pipette and holding pipette were bent to an angle of about 30° at the position of about 5 mm from the tip and then connected to a micromanipulator (LEITZ). The chamber used for the micromanipulation was a perforated slide glass with a cover glass, to which the cover glass was glued with yellow wax. Two drops of HEPES-buffered Whitten's medium supplemented with about 20 μl of 5% FCS were placed thereon. The surfaces of the drops were covered with mineral oil (M8410, Sigma). In one of the drops, approximately 100 ES cells were placed. Ten to fifteen expanded blastocysts were placed in the other drop. Ten to fifteen ES cells were injected per embryo.

All micromanipulation was carried out under an inverted microscope. After culturing for 1 to 2 hours, the manipulated embryos were transplanted into the uterine horn of ICR recipient females on the second day of pseudopregnancy. When no offspring were delivered on the expected date of delivery, the recipient females were subjected to Caesarean operation, and foster parents were used to raise the offspring. ES cells 2B7 were injected into 160 blastocysts from C57BL/6J mice collected on the 4th day of natural mating by flushing the uterus and as a result, 123 blastocysts survived with a success rate of 77%. These 123 blastocysts were transplanted into the uterine horn of ICR recipient females on the second day of pseudopregnancy, upon which 103 were found to be implanted and 95 offspring were obtained. Of the 83 offspring which became weaned, 30 were judged by their coat color to be chimeric mice, and 26 of these mice were morphologically male. The contribution rate of ES cells in these chimeric mice ranged from 10 to 95%, having a contribution ratio of less than 60% in 10 cases, from 60% or higher to less than 90% in 14 cases, and 90% or higher in 2 cases.

(b) The chimeric mice obtained were crossed with C57BL/6J mice. It was determined whether the delivered offspring (F1 heterozygous mice) were derived from the GLAST (GluT-1) gene-deficient ES cells. When the germ cells of the chimeric mice are derived from the ES cells, then the coat color of the delivered offspring are an agouti color, and when the offspring are derived from the blastocysts of C57BL/6J mice, they are a black color. To date, of the 9 chimeric mice (Nos. 1, 5, 13, 20, 33, 41, 54, 62 and 81) having a higher contribution rate (70% or higher) of the ES cells, the germ line transmission of the ES cells has been confirmed for 8 cases (Nos. 1, 5, 20, 33, 41, 54, 62 and 81).

Upon mating of No. 5 with a C57BL/6J female mouse, a total of 23 offspring were obtained in 3 deliveries, of which 23 exhibited an agouti coat color. Also, of the 15 offspring obtained by mating of No. 33 with a C57BL/6J female mouse, 12 were the agouti coat color. Of these mice with the agouti color, 23 were analyzed by southern blotting and 11 mice were confirmed to lack the GLAST (GluT-1)-1 gene.

(5) Backcrossing with C57BL/6J Strain Mouse

F1 heterozygous male mouse, which was confirmed to be deficient in the GLAST gene, was mated with a C57BL/6J wild type female mouse to obtain offspring. The genotype was analyzed by southern blotting to select a next generation heterozygous male mouse confirmed to be deficient in the GLAST gene. The heterozygous male mouse was again mated with the C57BL/6J female mouse to obtain a heterozygous male mouse for the next generation. As such, a total of 9 matings were repeated generation after generation to generate the GLAST gene-deficient heterozygous female and male mice of renewed generation. Finally, the heterozygous female and male mice were crossed with each other thereby to obtain GLAST knockout mice homozygous for GLAST gene deficiency (GLAST−/−), GLAST knockout mice heterozygous for GLAST gene deficiency (GLAST+/−), and wild type mice (GLAST+/+). These mice were used for the following measurement.

Example 2

Measurement of Intraocular Pressure

At the age of 1 year old, the intraocular pressure was measured in the homozygous GLAST knockout mice obtained in EXAMPLE 1 and wild type normal mice. After four mice per group were anesthetized, the intraocular pressure was measured with an electronic tonometer. The results are shown below.

Wild-type normal mice: 19±4 mmHg
Homozygous knockout mice: 15±3 mmHg
(mean±standard deviation)

From the results, it was confirmed that the intraocular pressure of homozygous GLAST knockout mice was within the normal pressure.

Example 3

Measurement of the Number of Cells in the Retinal Ganglions

In the homozygous GLAST knockout mice and heterozygous GLAST knockout mice obtained in EXAMPLE 1 and wild-type normal mice, the number of cells in the retinal ganglions was measured in each mouse by the hematoxylin/eosin staining of retinal sections and the retrograde labeling of retinal nerve cells by Fluoro-Gold or DiI.

Observation by Section Staining:

1) Test mice were anesthetized for sedation with a 1:1 mixture of ketamine (10 mg/ml)/medetomidine (1 mg/ml) (0.15-0.2 ml/mouse) and perfused in 4% paraformaldehyde to fix.

2) Eye globes were enucleated and fixed at 4° C. in the same solution for further 2 hours.

3) After the eye globes were embedded in paraffin, sections, e.g., 7 μm thick sections were prepared.

Figure 3:
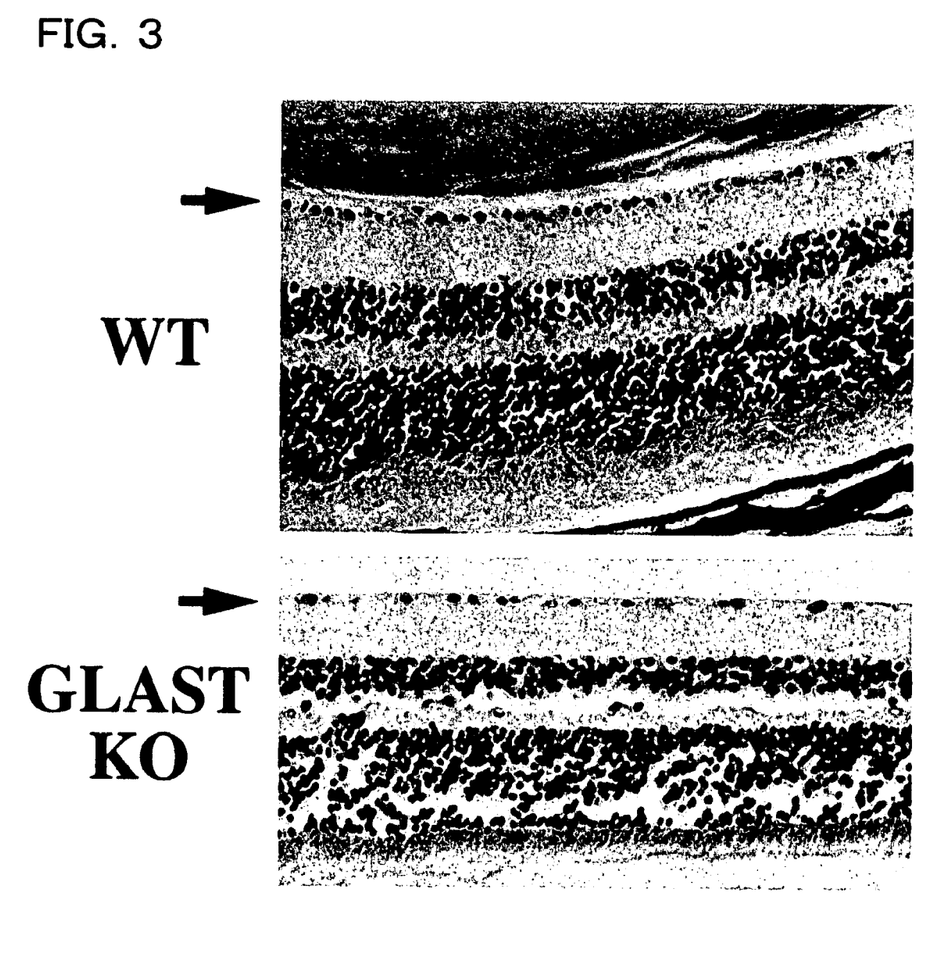
FIG. 3 shows the images of pathological sections in the retina of homozygous GLAST knockout mice (GLAST−/−) and wild-type normal mice (GLAST+/+).

4) The sections were stained with hematoxylin/eosin and the nerve cells in the retinal ganglion region were observed under microscope. The microscopic images are shown in FIG. 3.

5) The number of nerve cells in the section containing the retinal ganglion segment was counted in each mouse. The results are shown in FIG. 4.

Observation by Retrograde Labeling:

1) Mice were anesthetized for sedation with a 1:1 mixture of ketamine (10 mg/ml)/medetomidine (1 mg/ml) (0.15-0.2 ml/mouse) and then placed in a stereotaxic head frame.

2) After spraying ethanol under microscope, an incision was made with scissors along the midline of the head, exposing the skull.

3) After confirming sutures and blood vessels, holes for operation were drilled with a grinder and through the holes, Fluoro-Gold or DiI was injected into the superior colliculi.

4) After the skin was fastened with clips, atipamezole (5 mg/ml) (0.15-0.2 ml/mouse) was intraperitoneally injected and the recovery was ensured.

5) Following normal breeding for 7 days after the operation, the treated mice were anesthetized with ether resulting in death and the eye globes were enucleated. The anterior part of the eye was then removed.

6) The posterior part of the eye including the retina was placed in a solution of 4% paraformaldehyde and fixed at 4° C. for 20 minutes.

7) The retina was taken out and a whole-mount preparation was made.

Figure 5:
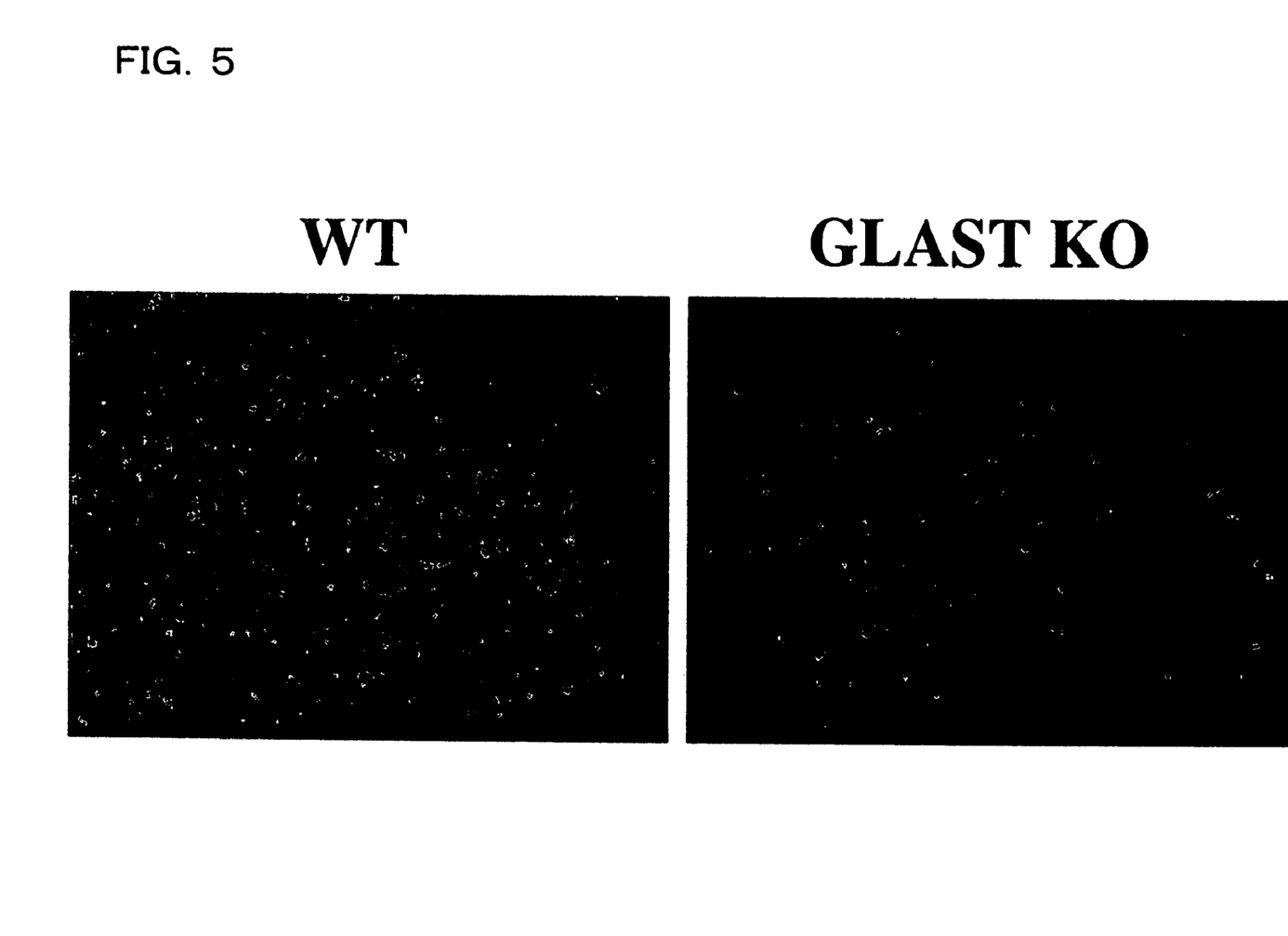
FIG. 5 shows the fluorescence images representing nerve cells labeled with Fluoro-Gold by retrograde labeling in the retinal ganglions of homozygous GLAST knockout mice (GLAST−/−) and wild-type normal mice (GLAST+/+).

8) Photographs of images of the fluorescence-labeled cells were taken with a fluorescence microscope. The images are shown in FIG. 5.

These results (FIGS. 3 to 5) revealed that in the homozygous GLAST knockout mice, the number of nerve cells in the retinal ganglions was significantly reduced, when compared with the wild-type mice and heterozygous knockout mice. The results of the hematoxylin/eosin staining (FIG. 3) indicates the reduced number of cells in the retinal ganglions, which are shown by arrows. Also, the reduction in the number of cells (amacrine cells, bipolar cells, etc.) located at the center and skin thinning in the inner nuclear layer accompanied by the reduction were observed. In addition, it was found that though the number of cells was reduced in the homozygous GLAST knockout mice when they were born, the number of cells was reduced also in the heterozygous knockout mice with passage of time, indicating a significant reduction with the age of 5 weeks or after, when compared with the wild-type mice (FIG. 4).

INDUSTRIAL APPLICABILITY

The endogenous GLAST gene-deficient homozygous or heterozygous GLAST knockout mouse of the invention, as a model mouse for normal tension glaucoma, is expected to be extremely useful for developing therapeutics effective for the treatment of said disease, establishing a remedy therefor and identifying the cause of said disease or its onset mechanism.

---

The invention claimed is:

1. A GLAST knockout mouse deficient in the function of an endogenous GLAST gene, wherein said mouse has the same genome, except for the targeted endogeneous GLAST gene, as that of a C57BL/6 mouse strain, and wherein, when ischemic load is not applied:
   1) the intraocular pressure is not greater than 21 mmHg, and,
   2) the number of cells in the retinal ganglions is 20% to 50% less than that of a wild-type C57BL/6 strain mouse.

2. The GLAST knockout mouse according to claim 1, wherein a neomycin-resistant gene is inserted into a region of the endogenous GLAST gene.

3. The GLAST knockout mouse according to claim 2, wherein the neomycin-resistant gene is inserted into the exon 6 of the endogenous GLAST gene.

4. A method of producing a GLAST knockout mouse deficient in the function of an endogenous GLAST gene, which comprises the following steps 1) to 6):
   1) obtaining an ES cell from any mouse deficient in the function of one endogenous GLAST gene on the homologous chromosome,
   2) introducing the ES cell obtained in step 1 into the mouse to generate a chimeric mouse carrying said cell,
   3) crossing the chimeric mouse obtained in step 2 with a normal C57BL/6 4strain mouse to obtain a heterozygous knockout mouse,
   4) crossing the heterozygous mouse obtained in step 3 with a normal C57BL/6 strain mouse to generate a heterozygous knockout mouse,
   5) repeating the crossing defined in step 4 at least a total of 9 times to generate a heterozygous knockout mouse, and,
   6) crossing the heterozygous knockout mice obtained in step 5 with each other to generate a homozygous or heterozygous GLAST knockout mouse.

5. A homozygous or heterozygous GLAST knockout mouse, wherein said mouse has the same genome, except for the targeted endogeneous GLAST gene. as that of a CS7BL/6 mouse strain, and wherein:
   1) the intraocular pressure is not greater than 2 mmHg and
   2) the number of cells in the retinal ganglions is 20% to 50% less than that of a wild-type C57BL/6 mouse strain, and
   produced by the production method which comprises the following steps 1) to 6):
   1) obtaining an ES cell from any mouse deficient in the function of one endogenous GLAST gene on the homologous chromosome,
   2) introducing the ES cell obtained in step 1 into the mouse to generate a chimeric mouse carrying said cell,
   3) crossing the chimeric mouse obtained in step 2 with a normal C57BL/6 strain mouse to obtain a heterozygous knockout mouse,
   4) crossing the heterozygous mouse obtained in step 3 with a normal C57BL/6 mouse strain to generate a heterozygous knockout mouse,
   5) repeating the crossing defined in step 4 at least a total of 9 times to generate a heterozygous knockout mouse, and,
   6) crossing the heterozygous knockout mice obtained in step 5 with each other to generate a homozygous or heterozygous GLAST knockout mouse.

6. A method of screening a compound for potential use in the prevention and/or treatment of normal tension glaucoma, which comprises:
   1) administering a test compound to the GLAST knockout mouse according to claim 2,
   2) administering a test compound to a wild-type mouse,
   3) assessing the number or function of surviving optic nerve cells in each of the mice defined above, prior to and after a given time period of the administration, and,
   4) comparing the GLAST knockout mouse with the wild-type mouse in terms of the test results to determine effectiveness of the test compound.

7. The screening method according to claim 6, wherein the number of nerve cells in the retinal ganglions is counted and/or the retinal potential is measured to assess the number of surviving optic nerve cells or the function of optic nerve cells.

* * * * *

SEQUENCE LISTING

```
<160> NUMBER OF SEQ ID NOS: 2

<210> SEQ ID NO 1
<211> LENGTH: 1629
<212> TYPE: DNA
<213> ORGANISM: Mouse

<400> SEQUENCE: 1
atgaccaaaa gcaacggaga agagcctagg atgggggca ggatggagag attgcagcaa      60
ggggtccgca agcggacact tctggccaag aagaaagttc agagcctcac caaggaagat     120
```

```
gttaagagtt acctgtttcg gaatgccttc gttctgctca cggtcactgc tgtcattgtg    180
ggtacaatcc ttggatttgc cctccgaccg tataaaatga gctaccggga ggtgaagtac    240
ttttcgttcc ctggggagct tctcatgagg atgctgcaga tgctggtctt gcccctgatc    300
atctccagtc tcgtcacagg aatggcggcc ctagatagta aggcatccgg aagatgggg     360 atgcgcgctg tagtctatta catgactact accatcattg ctgtggtgat tggcataatc    420
attgtcatca tcatccaccc cggaaagggc acaaggaaa acatgtacag agaaggtaaa     480
atcgtgcagg tcactgcagc agatgccttc ctggatttga tcaggaacat gttccctccc    540
aatctggtag aagcctgctt taaacagttt aaaaccagct acgagaaaag aagctttaaa    600
gtgcctatcc agtccaacga aacacttctg ggcgccgtga tcaacaacgt gtcagaggcc    660
atggagactc tgacccggat ccgggaggag atggtgcccg tgcctggatc tgtgaatggg    720
gtcaatgccc tgggcctagt tgtcttctcc atgtgcttcg gtttcgtgat cggaaacatg    780
aaggagcagg ggcaagcgct gagagagttc tttgattctc ttaacgaagc catcatgcga    840
ttggtcgcgg tgataatgtg gtatgcgcct ctgggcatcc tcttcttgat cgcaggaag     900 attgttgaga tggaagacat gggtgtgatt gggggacagc ttgccatgta caccgtgaca    960
gtcattgtcg gcctcctcat tcacgccgtc atcgtcctgc ctctcctcta cttcctggta    1020
acccggaaga cccctgggt tttcattgga gggttgctgc aagcgctcat cacagccctt    1080
gggacctcct caagttctgc caccctaccc atcactttca agtgcctgga agagaacaat    1140
ggtgtggaca aacgcatcac cagatttgtg ctccccgtgg gggccaccat taacatggat    1200
gggaccgccc tctacgaggc tttggctgcc attttcatcg ctcaagtgaa caactttgac    1260
ctgaactttg gacagattat aacaataagc atcacagcca cggccgcaag catcggggca    1320
gccgggattc ctcaggccgg tctggtcacc atggtcatcg tgctgacatc tgtgggcctg    1380
cccacagatg acatcacact catcattgca gtggactggt ttctggaccg cctccgaacc    1440
accaccaacg tactgggtga ctccctcgga gcagggattg tcgagcactt gtcccgacat    1500
gaactgaaga accgagatgt tgaaatgggg aactcggtga ttgaggagaa cgaaatgaag    1560
aagccgtatc agctgattgc ccaggacaat gaaccggaga aacccgtggc agacagcgaa    1620
accaagatg                                                            1629
```

<210> SEQ ID NO 2
<211> LENGTH: 543
<212> TYPE: PRT
<213> ORGANISM: Mouse

<400> SEQUENCE: 2

Met Thr Lys Ser Asn Gly Glu Glu Pro Arg Met Gly Gly Arg Met Glu
1               5                   10                  15

Arg Leu Gln Gln Gly Val Arg Lys Arg Thr Leu Leu Ala Lys Lys
            20                  25                  30

Val Gln Ser Leu Thr Lys Glu Asp Val Lys Ser Tyr Leu Phe Arg Asn
        35                  40                  45

Ala Phe Val Leu Leu Thr Val Thr Ala Val Ile Val Gly Thr Ile Leu
    50                  55                  60

Gly Phe Ala Leu Arg Pro Tyr Lys Met Ser Tyr Arg Glu Val Lys Tyr
65                  70                  75                  80

Phe Ser Phe Pro Gly Glu Leu Leu Met Arg Met Leu Gln Met Leu Val
                85                  90                  95

```
Leu Pro Leu Ile Ile Ser Ser Leu Val Thr Gly Met Ala Ala Leu Asp
            100                 105                 110

Ser Lys Ala Ser Gly Lys Met Gly Met Arg Ala Val Tyr Tyr Met
        115                 120                 125

Thr Thr Thr Ile Ile Ala Val Val Ile Gly Ile Ile Val Ile Ile
            130                 135                 140

Ile His Pro Gly Lys Gly Thr Lys Glu Asn Met Tyr Arg Glu Gly Lys
145                 150                 155                 160

Ile Val Gln Val Thr Ala Ala Asp Ala Phe Leu Asp Leu Ile Arg Asn
                165                 170                 175

Met Phe Pro Pro Asn Leu Val Glu Ala Cys Phe Lys Gln Phe Lys Thr
            180                 185                 190

Ser Tyr Glu Lys Arg Ser Phe Lys Val Pro Ile Gln Ser Asn Glu Thr
        195                 200                 205

Leu Leu Gly Ala Val Ile Asn Asn Val Ser Glu Ala Met Glu Thr Leu
            210                 215                 220

Thr Arg Ile Arg Glu Glu Met Val Pro Val Pro Gly Ser Val Asn Gly
225                 230                 235                 240

Val Asn Ala Leu Gly Leu Val Val Phe Ser Met Cys Phe Gly Phe Val
                245                 250                 255

Ile Gly Asn Met Lys Glu Gln Gly Gln Ala Leu Arg Glu Phe Phe Asp
            260                 265                 270

Ser Leu Asn Glu Ala Ile Met Arg Leu Val Ala Val Ile Met Trp Tyr
        275                 280                 285

Ala Pro Leu Gly Ile Leu Phe Leu Ile Ala Gly Lys Ile Val Glu Met
            290                 295                 300

Glu Asp Met Gly Val Ile Gly Gly Gln Leu Ala Met Tyr Thr Val Thr
305                 310                 315                 320

Val Ile Val Gly Leu Leu Ile His Ala Val Ile Val Leu Pro Leu Leu
                325                 330                 335

Tyr Phe Leu Val Thr Arg Lys Asn Pro Trp Val Phe Ile Gly Gly Leu
            340                 345                 350

Leu Gln Ala Leu Ile Thr Ala Leu Gly Thr Ser Ser Ser Ser Ala Thr
        355                 360                 365

Leu Pro Ile Thr Phe Lys Cys Leu Glu Glu Asn Asn Gly Val Asp Lys
370                 375                 380

Arg Ile Thr Arg Phe Val Leu Pro Val Gly Ala Thr Ile Asn Met Asp
385                 390                 395                 400

Gly Thr Ala Leu Tyr Glu Ala Leu Ala Ala Ile Phe Ile Ala Gln Val
                405                 410                 415

Asn Asn Phe Asp Leu Asn Phe Gly Gln Ile Ile Thr Ile Ser Ile Thr
            420                 425                 430

Ala Thr Ala Ala Ser Ile Gly Ala Ala Gly Ile Pro Gln Ala Gly Leu
        435                 440                 445

Val Thr Met Val Ile Val Leu Thr Ser Val Gly Leu Pro Thr Asp Asp
            450                 455                 460

Ile Thr Leu Ile Ile Ala Val Asp Trp Phe Leu Asp Arg Leu Arg Thr
465                 470                 475                 480

Thr Thr Asn Val Leu Gly Asp Ser Leu Gly Ala Gly Ile Val Glu His
                485                 490                 495

Leu Ser Arg His Glu Leu Lys Asn Arg Asp Val Glu Met Gly Asn Ser
        500                 505                 510
```

```
Val Ile Glu Glu Asn Glu Met Lys Lys Pro Tyr Gln Leu Ile Ala Gln
        515                 520                 525

Asp Asn Glu Pro Glu Lys Pro Val Ala Asp Ser Glu Thr Lys Met
    530                 535                 540
```